(12) United States Patent
Niewczas et al.

(10) Patent No.: US 7,066,008 B2
(45) Date of Patent: Jun. 27, 2006

(54) METHOD FOR MEASURING CONCENTRATION OF SOLID OR LIQUID PARTICULATE MATTER IN A GASEOUS CARRIER MEDIUM

(75) Inventors: Bogdan Niewczas, Balice (PL); Mariusz Randak, Krakow (PL); Paulina Piwowarczyk, Krakow (PL); Tomasz Piwowarczyk, Krakow (PL)

(73) Assignee: Zaklad Aparatury Pomiarowet Kwant Sp z.o.o., Cracow (PL)

( * ) Notice: Subject to any disclaimer, the term of this patent is extended or adjusted under 35 U.S.C. 154(b) by 111 days.

(21) Appl. No.: 10/932,467

(22) Filed: Sep. 2, 2004

(65) Prior Publication Data
US 2005/0257601 A1    Nov. 24, 2005

(51) Int. Cl.
*G01N 22/00* (2006.01)
(52) U.S. Cl. .................................. 73/24.03; 73/28.01
(58) Field of Classification Search ........... 73/23.03, 73/28.01; 702/24, 49
See application file for complete search history.

(56) References Cited

U.S. PATENT DOCUMENTS

| | | | |
|---|---|---|---|
| 5,177,444 A | * | 1/1993 | Cutmore .................... 324/637 |
| 5,729,470 A | * | 3/1998 | Baier et al. ................... 702/24 |
| 6,109,097 A | * | 8/2000 | Conrads et al. ............. 73/61.41 |
| 6,119,510 A | * | 9/2000 | Carasso et al. ............. 73/61.75 |
| 6,490,909 B1 | * | 12/2002 | Boguszewski et al. ..... 73/23.33 |

FOREIGN PATENT DOCUMENTS

| EP | 0 717 269 A3 | 6/1996 |
|---|---|---|
| WO | WO 99/01752 | 1/1999 |

\* cited by examiner

*Primary Examiner*—Hezron Williams
*Assistant Examiner*—Ryan Christensen
(74) *Attorney, Agent, or Firm*—Patricia M. Mathers; Thomas L. Bohan

(57) ABSTRACT

A method of measuring concentration of solid or liquid particulate matter in a gaseous carrier medium, particularly suitable for measuring concentration and flow rate of pulverized fuel pneumatically transported in a duct to power station boiler burners. The method includes generating a radio frequency electromagnetic wave within a duct, measuring wave parameters within a range of frequencies, including a cut-off frequency, determining the cut-off frequency from changes in wave parameters, calculating dielectric permittivity of a two-phase flow duct load, and ascribing to this value a corresponding concentration value. The measured parameter is the rate of change of phase shift against frequency at two arbitrary points on a wave transmission path, whereas the waveguide cut-off frequency value is determined at a point where the rate of change of phase shift against frequency reaches a maximum.

11 Claims, 4 Drawing Sheets

METHOD FOR MEASURING CONCENTRATION OF SOLID OR LIQUID PARTICULATE MATTER IN A GASEOUS CARRIER MEDIUM

BACKGROUND INFORMATION

1. Field of the Invention

The object of this invention is to provide a method for measuring the concentration of solid or liquid particulate matter suspended in a gaseous carrier medium; a particular application being the measurement of concentration and flow rate of pulverised solid fuel pneumatically transported in a duct to power station boiler burners.

2. Description of the Prior Art

There already exist methods for measuring the concentration of particulate matter in a gaseous carrier medium: these exploit the effect of particulate matter concentration on the parameters of radio frequency (RF) electromagnetic radiation transmitted along the duct transporting the particulate matter. Also, the established physical principle states that at a precisely specified frequency, known as the cut-off frequency, a step change in the electromagnetic radiation parameters can be detected—the step change being a transition from attenuation to propagation mode. The value of the cut-off frequency depends upon the physical properties of the duct and on the waveguide geometry.

One specific method of measurement utilising the principle described above is presented in a Polish patent application no. P-337795 (WO9901752). This particular method is based on an RF electromagnetic wave being transmitted along a duct (which acts as a waveguide). Subsequently, at a point in the duct axially remote from the transmission point, the attenuation of the signal is continuously measured at a frequency below the cut-off frequency. The change of the cut-off frequency value is derived by making a mathematical comparison between a range of attenuation curves defined for the actual measurement conditions and a range of attenuation curves obtained under calibration conditions for the flow of particulate matter of known concentration. Usually, the calibration process is carried out using clean air. Subsequently, the dielectric permittivity $\in_1$ of mixed carrier gas and suspended particulate matter is derived from the following formula:

$$\in_1 = 1/\mu_1 (1 - \Delta f_g / f_{go})^2,$$

which is derived from the conversion of the following equation:

$$\Delta f_g = f_{go} - f_{g1} = f_{go}(1 - 1/\sqrt{\mu_1 \in_1}),$$

wherein:

$\Delta f_g$—the cut-off frequency shift between calibration conditions $f_{go}$ and actual measurement conditions $f_{g1}$ $\mu_1$—magnetic permeability of mixed carrier gas and suspended particulate matter.

Thus from the derived dielectric permittivity $\in_1$, a corresponding value for the concentration of the particulate matter can be calculated.

In case of the aforedescribed method, the accuracy with which the concentration of particulate matter within the duct or waveguide depends on the accurate estimation of cut-off frequency values. Attenuation measurement is based on measuring and comparing the amplitude of the RF electromagnetic wave at a point where it is generated and at a second point axially remote from the first position. The achievable accuracy of these measurements proves insufficient to properly determine the flow rate of pneumatically transported particulate matter. Furthermore, it must be pointed out that the "synthesized" relationship between the measured attenuation and the shift in cut-off frequency, as it is represented by the derived mathematical model curves, is not identical to the actual relationship observed by comparing the cut-off frequency shift caused by the change of concentration of particulate matter in actual flow conditions with the flow conditions measured when the concentration of particulate matter is known. The slope of these substantially linear sections is a function of dielectric permittivity and conductivity of the two-phase flow: if the linear sections are out-of-parallel, this may yield strongly distorted measurement results.

BRIEF SUMMARY OF THE INVENTION

The measurement methodology described in the present invention is different from the previously described method in that the measured RF electromagnetic wave parameter is the rate of change of phase shift against frequency measured between two arbitrary points along the transmission path of the electromagnetic wave, and the waveguide cut-off frequency value is determined at a point where the rate of change of phase shift against frequency reaches a maximum.

The value of dielectric permittivity is derived from the following equation:

$$\varepsilon_1 = \left(\frac{1,81118c}{2\pi r f_{gI}}\right)^2 \frac{1}{\mu_1}$$

wherein:

$f_{g1}$ is wave cut-off frequency, r is duct radius, $\mu_1$ is magnetic permeability of the two-phase flow, $\in_1$ is dielectric permittivity of the two-phase flow, c is the speed of light.

Currently used measurement and calculation methods enable very accurate, direct measurement of RF electromagnetic wave phase shift. The analysis of the waveguide properties within a range of frequencies including the cut-off frequency shows that at the cut-off frequency the RF wave in an ideal, unimpeded two-phase flow of carrier gas and particulate matter reaches infinite phase velocity, whereas in a real, frictional two-phase flow, phase velocity reaches a maximum. This is represented by the fact that the rate of change of phase shift between two points of RF wave propagation reaches a maximum value. It is assumed that magnetic permeability $\mu_1=1$. The concentration of particulate matter is therefore determined from one direct measurement of the cut-off frequency; consequently, there is no need to calibrate the measuring system for the flow of particulate matter of known concentration.

The development of the present invention allows higher accuracy by determining the cut-off frequency for the flow of particulate matter of known concentration in the same way as it is done for the actual flow, and the dielectric permittivity is derived from the following equation:

$$\varepsilon_1 = \frac{1}{\mu_1 \left(1 - \frac{\Delta f_g}{f_{go}}\right)^2}$$

wherein:

$\mu_1$ is magnetic permeability of the two-phase flow in measurement conditions $\Delta f_g$ is cut-off frequency shift $\Delta f_g = f_{go} - f_{g1}$ $f_{go}$ is cut-off frequency for the flow conditions of suspended particulate matter of known concentration $f_{g1}$ is cut-off frequency in the actual flow conditions.

This method is recommended particularly in conditions where the flow of particulate matter causes a change of duct dimensions due to abrasive wear of its surfaces. Calibration measurement based on the flow of suspended particulate matter of known concentration increases the measurement accuracy by eliminating errors caused by dimensional changes. Preferably, the calibration measurement is carried out using the flow of clean air.

A further advantage offered by this invention is the elimination of measurement errors caused by the occurrence within the flow pattern of sections of increased density—or "roping" as it is called.

The measurement of the rate of change of phase shift between two points of the wave propagation, one set behind the other in relation to the direction of travel of the RF wave, is carried out by at least two sets of measuring probes, each consisting of a transmitting and receiving probe, orientated to lie within planes that intersect the axis of the transport duct. Preferably, the measuring sets are at 90° to each other around the duct's circumference.

Dielectric permittivity can be determined either by calculating the average value of cut-off frequencies or by calculating the difference between cut-off frequencies determined from the maximum rates of change of phase shift against frequency from all measuring sets.

An additional measurement of flow velocity enables the calculation, for a given concentration, of the flow rate of suspended particulate matter in a given duct.

The aforedescribed innovative idea is shared with another possibility of determining the value of cut-off frequency shift in a waveguide for the flow conditions of known particulate matter concentration and for the actual flow conditions, which utilizes the measurement of phase shift in two points of the RF wave propagation. This measurement is done within the frequency range including the cut-off frequency. The shift of the curve representing phase shift caused by the change of particulate matter concentration is substantially parallel, and therefore the slope of the curve is very stable.

Preferably, the cut-off frequency shift is calculated as a mean value of the shifts of at least two points of the curve, in the frequency range including the transition from wave attenuation to wave propagation.

Analogically to the aforedescribed method, errors connected with the occurrence in the flow pattern of sections of increased density ("roping") can be eliminated by measuring with at least two measuring sets, as well as using the mean value of curve points shift to calculate dielectric permittivity.

The methodology of the present invention will now be described by way of example, as a measurement of the flow parameters of pulverised fuel supplied to a power boiler burner. The written description is supported by the accompanying drawings, in which:

BRIEF DESCRIPTION OF THE DRAWINGS

The present invention is described with reference to the accompanying drawings.

DETAILED DESCRIPTION OF THE INVENTION

Figure 1:
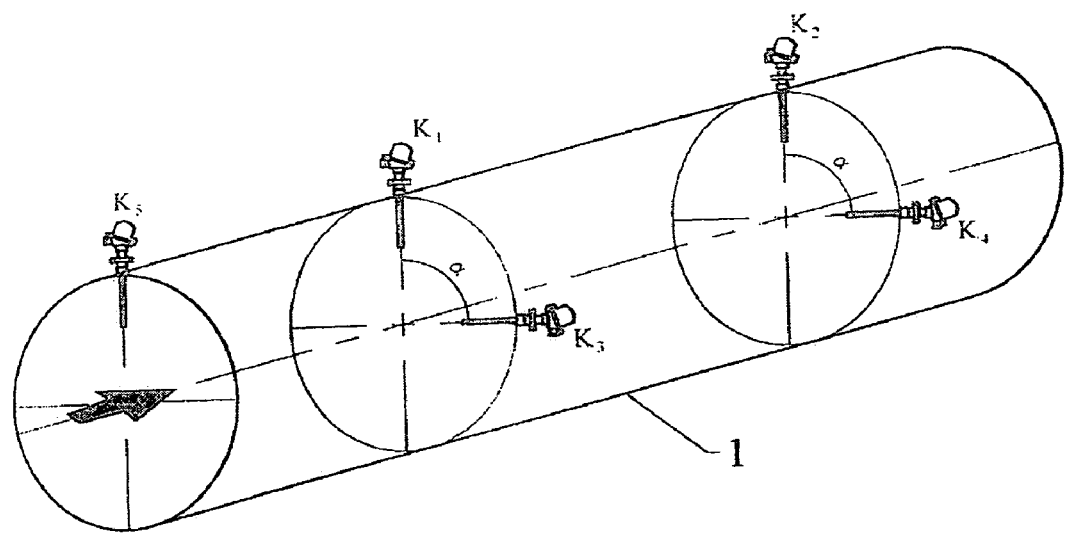
FIG. 1 shows the measuring section of a pulverised fuel duct.

FIG. 1 shows an arrangement of measuring probes k1, k2, k3, k4 and k5 fitted on a steel duct 1. Pulverised fuel is pneumatically transported in the steel duct 1 of circular cross-section with a diameter D=0.315 m. The measuring probes include two transmitting probes k1 and k3 as well as two receiving probes k2 and k4 that are arranged so as to enable the measurement of RF electromagnetic wave parameters. The k5 probe is used for the measurement of pulverised fuel velocity. All probes k1, k2, k3, k4 and k5 are connected to a control unit (not shown) responsible for the measurement and electronic conversion of data, enabling a precise determination of the first derivative of phase shift $\Delta \phi$ against frequency. The derivative $d(\Delta \phi)/df$ reaches a maximum at the value representing the cut-off frequency $f_g$.

Figure 2:
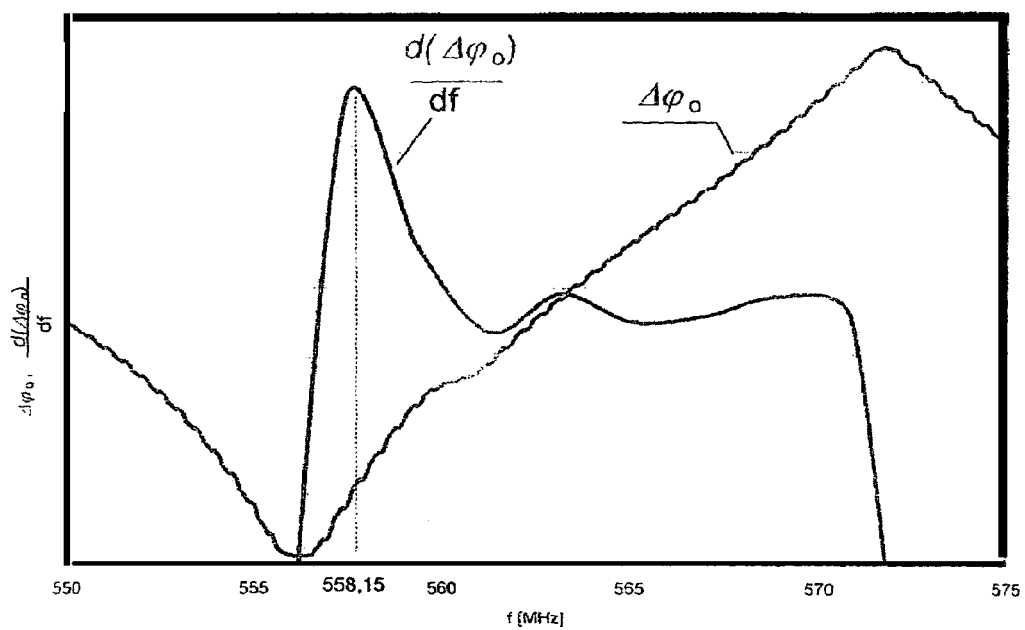
FIG. 2 shows the curves of electromagnetic wave phase shift and the rate of change of phase shift against frequency.

FIG. 2 shows an empirically determined phase shift $\Delta \phi_0$ curve of a wave in two points of the duct with air load only, and a curve showing the first derivative of phase shift against frequency $d(\Delta \phi_0)/df$. The frequency at which $d(\Delta \phi_0)/df$ reaches maximum is the cut-off frequency of a wave in a duct, which in this particular case is 558.15 MHz.

Figure 3:
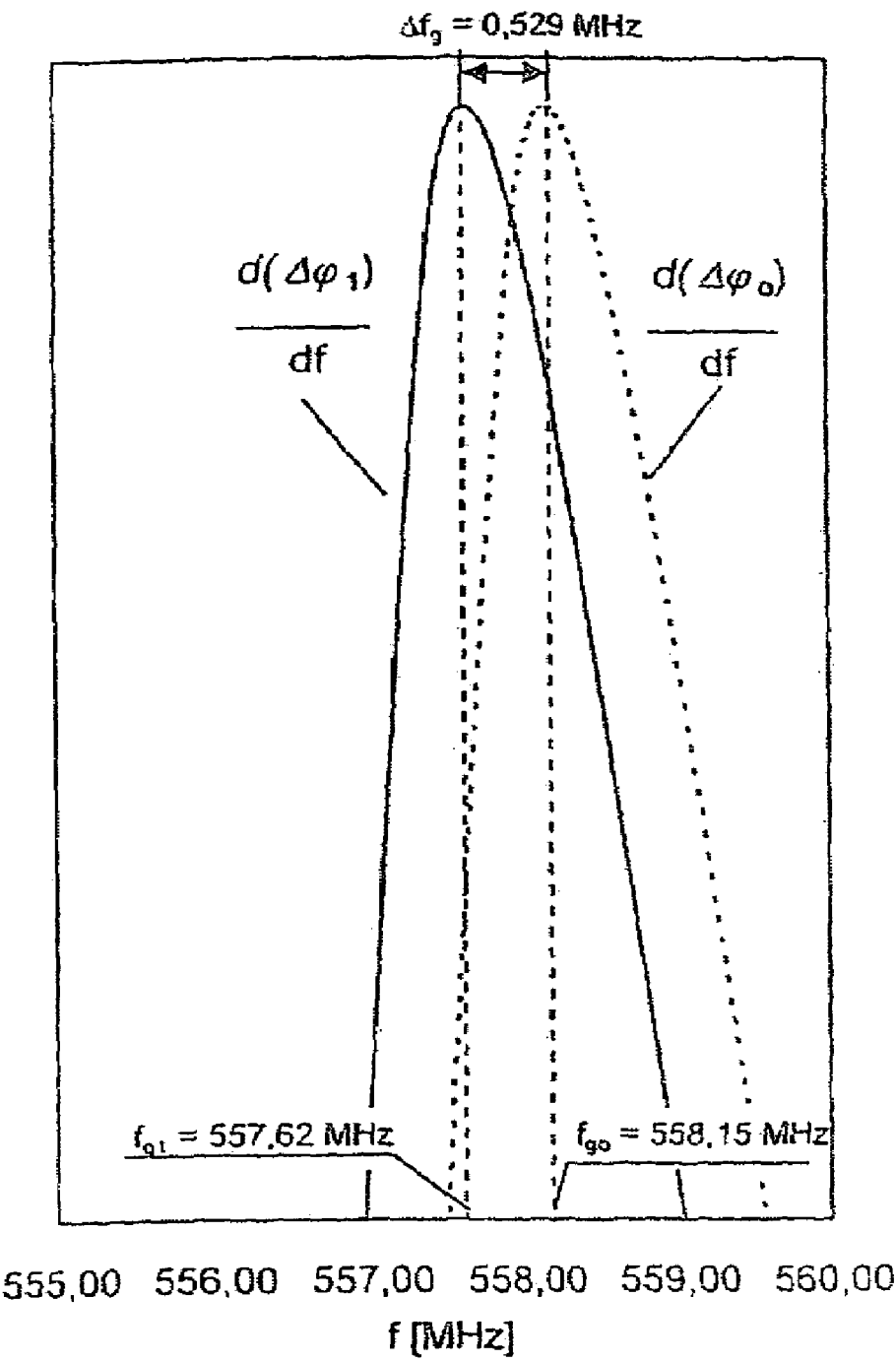
FIG. 3 shows empirically determined curves depicting the rate of change of phase shift in a duct carrying air only $\Delta \phi_0$, the rate of change of phase shift in a duct carrying pulverised fuel $\Delta \phi_1$.

FIG. 3 shows the determined curve $d(\Delta \phi_0)/df$ of an RF wave in a duct 1, at flow conditions of known particulate matter concentration. In this particular case, the duct was loaded with clean air only. Subsequently, the curve $d(\Delta \phi_1)/df$ of a wave in the duct 1 with pulverised fuel load was determined. The maximum values $d(\Delta \phi)/df$ occur at the cut-off frequencies. Based upon the value of a wave cut-off frequency shift $\Delta f_g$, or on the basis of a cut-off frequency value $f_{g1}$ of a wave in a duct with pulverised fuel load, a dielectric permittivity value $\varepsilon_1$ can be determined and, subsequently ascribed an appropriate pulverised fuel concentration value. In this demonstration case, the calculated values were as follows:

$\Delta f_g$=0.529 MHz, $f_g$=557.62 MHz,

Concentration of pulverised fuel=949 g/m$^3$.

The velocity of particulate matter, measured using the k5 probe, enabled the calculation of the pulverised fuel flow rate.

A second embodiment of particulate matter concentration measurement method is also presented as applied to a measurement of pulverised fuel flow parameters inside the steel duct 1 of a diameter D=0.315 m, as exemplified by FIG. 1.

Figure 4:
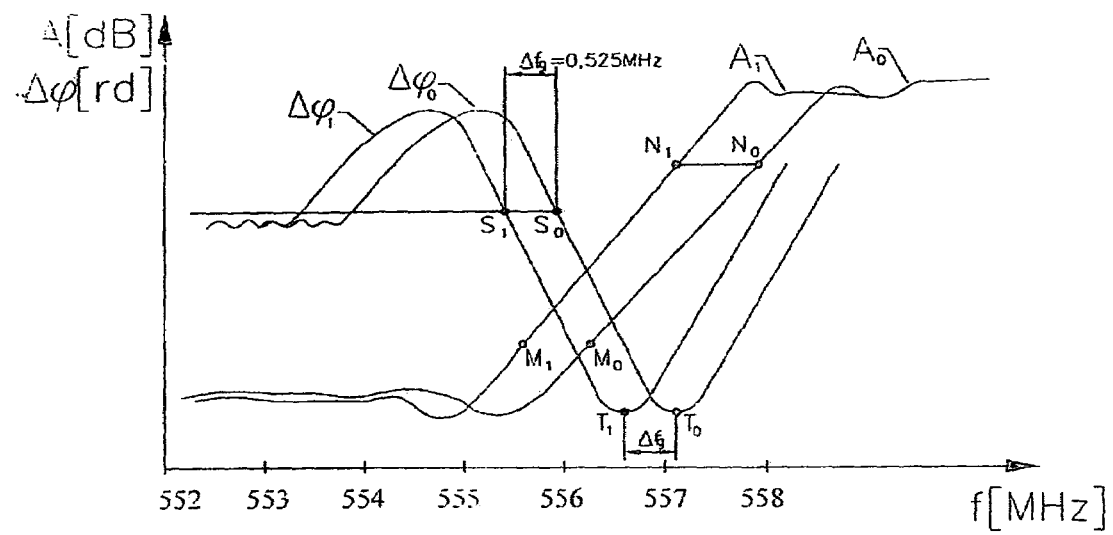
FIG. 4 shows the curves of intensity and phase shift within a duct.

FIG. 4 shows curves of RF electromagnetic wave intensity $A_0$ and $A_1$, and curves of phase shift $\Delta \phi_0$ and $\Delta \phi_1$. The $A_0$ and $\Delta \phi_0$ curves were achieved at air load only within the duct 1, whereas the $A_1$ and $\Delta\phi_1$ curves were achieved in the duct 1 loaded with pulverised fuel suspended in a stream of air. The slope of $A_0$ and $A_1$ curves exemplifies that substantially linear sections $M_0N_0$ and $M_1N_1$ are out of parallel: hence the calculation of the shift of the intensity curve against frequency may yield errors.

The value of the cut-off frequency shift has been determined in relation to the value of $\Delta\phi_1$ and $\Delta\phi_0$ phase shift against frequency. Hence, given the constant value of $\Delta\phi$, $S_0$ point is shifted to $S_1$ point by $\Delta\phi_g$ value=0.525 MHz.

From the following equation:

$$\in_1 = 1/\mu_1(1-\Delta f_g/f_{g0})$$

$\in_1$ is derived, and this particular value is then assigned the pulverised fuel concentration value which, in this particular case, is 942 g/m3. The value of the cut-off frequency $f_{g0}$ may be determined, by way of measurement, as frequency at which $$\frac{d(\Delta\varphi_0)}{df}$$

reaches a maximum.

What is claimed is:

1. A method of measuring the concentration of particulate matter suspended in a gaseous carrier medium whilst transported via a duct made of electrically conductive material, said method comprising the steps:
   (a) generating a radio frequency electromagnetic wave within the duct,
   (b) measuring wave parameters across a range of frequencies, including a wave cut-off frequency, at two arbitrary points on a wave transmission path the two arbitrary points lying in a plane that intersects both a duct axis and a wave generation point,
   (c) determining the wave cut-off frequency, based on changes in wave parameters, and
   (d) calculating a value of dielectric permittivity of a two-phase flow of a carrier gas and a particulate matter with which the duct is loaded and ascribing to this value of dielectric permittivity a corresponding value of a particulate matter concentration in actual flow conditions,
   wherein measured wave parameters include a rate of change of phase shift in two points along a wave propagation $(d(\Delta\phi_1)/df)$, and
   wherein a value of a waveguide cut-off frequency $(f_{g1})$ is determined as a value at which the rate of change of phase shift against frequency $(d(\Delta\phi_1)df)$ reaches a maximum, and the value of dielectric permittivity $(\in_1)$ is derived from a dielectric permittivity formula $$\varepsilon_1 = \left(\frac{1,81118c}{2\pi r f_{g1}}\right)^2 \frac{1}{\mu_1}.$$

2. The method according to claim 1, wherein the cut-off frequency is determined for a flow of particulate matter of known concentration in the same way as it is done for the actual flow, and the dielectric permittivity $(\in_1)$ is derived from the following equation:

$$\varepsilon_1 = \frac{1}{\mu_1\left(1-\frac{\Delta f_g}{f_{g0}}\right)^2}.$$

3. The method according to claim 2, wherein the value of the cut-off frequency $(f_{go})$ for the flow of particulate matter of known concentration is determined for a flow of clean air.

4. The method according to claim 2, wherein the measurements of the rate of change of phase shift against frequency in two points along the wave propagation $(d(\Delta\phi_1)/df)$ are carried out using at least two measuring probe sets, each measuring probe set including a transmitting probe and a receiving probe that is fitted in a plane that intersects the duct axis of the transport duct;
   wherein permittivity $(\in_1)$ is determinable either by calculating an average value of wave cut-off frequencies $(f_g)$ or by calculating cut-off frequency shifts $(\Delta f_g)$ determined on the basis of measurements from all measuring sets.

5. The method according to claim 4, wherein the measuring probe sets (k1, k2 and k3, k4) are positioned at 90° against each other around the circumference of the duct.

6. The method according to claim 1, further including the steps of measuring a velocity of suspended pulverised matter with a velocity probe (k5) and, on the basis of concentration and velocity, calculating a flow rate of pulverised matter suspended in a gaseous carrier medium.

7. A method of measuring the concentration of particulate matter suspended in a gaseous carrier medium whilst transported via a duct made of electrically conductive material, said method comprising the steps:
   (a) generating an electromagnetic wave within the duct,
   (b) measuring wave parameters across a range of frequencies including the cut-off frequency at two arbitrary points on the wave transmission path which lie in a plane intersecting both the duct axis and the wave generation point,
   (c) based on changes in wave parameters, determining a cut-off frequency shift for flow conditions of a particulate material of known concentration and for actual flow conditions, and
   (d) deriving a value of dielectric permittivity $\in_1$ from a dielectric permittivity equation $\in_1=1/\mu_1(1-\Delta f_g/f_{go})^2$, and ascribing to thus calculated dielectric permittivity $(\in_1)$, a corresponding concentration value of the particulate matter,
   wherein a parameter determining the difference between cut-off frequency values $(\Delta f_g)$ is a value of the phase shift against frequency, represented by $(S_0, S_1)$ section, of a selected $S_0$ point on a phase shift curve $(\Delta\phi_0)$, measured in two points of a wave propagation $(k_1)$ and $(k_2)$; the shift being caused by a change in a concentration value from a known concentration value to an actual concentration value.

8. The method according to claim 7, wherein the cut-off frequency shift $(\Delta f_g)$ is determined as a mean value of the shifts against frequency, section $(S_0, S_1)$ and section $(T_0, T_1)$ of at least two points $(S_0, T_0)$ of the curve of wave phase shift $\Delta\phi_0$; the shifts being caused by the change in concentration value of particulate matter from the known concentration value to the actual concentration value.

9. The method according to claim 8, wherein measurements of shifts against frequency of points on a phase difference curve are done using at least two measuring sets, each measuring set including a transmitting probe (k1, k3) and a receiving probe (k2, k4), orientated to lie within planes that intersect the axis of the transport duct; and wherein dielectric permittivity ($\epsilon_1$) is calculated using the average value of cut-off frequency shifts ($\Delta f_g$), determined on the basis of phase shifts ($\Delta \phi_g$) in all measuring sets.

10. The method according to claim 9, wherein the measuring sets (k1, k2 and k3, k4) are positioned at 90° to each other around the circumference of the duct.

11. The method according to claim 7, further including the step of measuring the velocity of transported particulate matter with a velocity probe (k5) and, on the basis of concentration and velocity, calcuating the flow rate of pulverised matter suspended in a gaseous carrier medium.

* * * * *